Dec. 21, 1954 F. C. CHANDLER Plant Pat. 1,334
MAGENTA VERBENA PLANT
Filed March 12, 1954
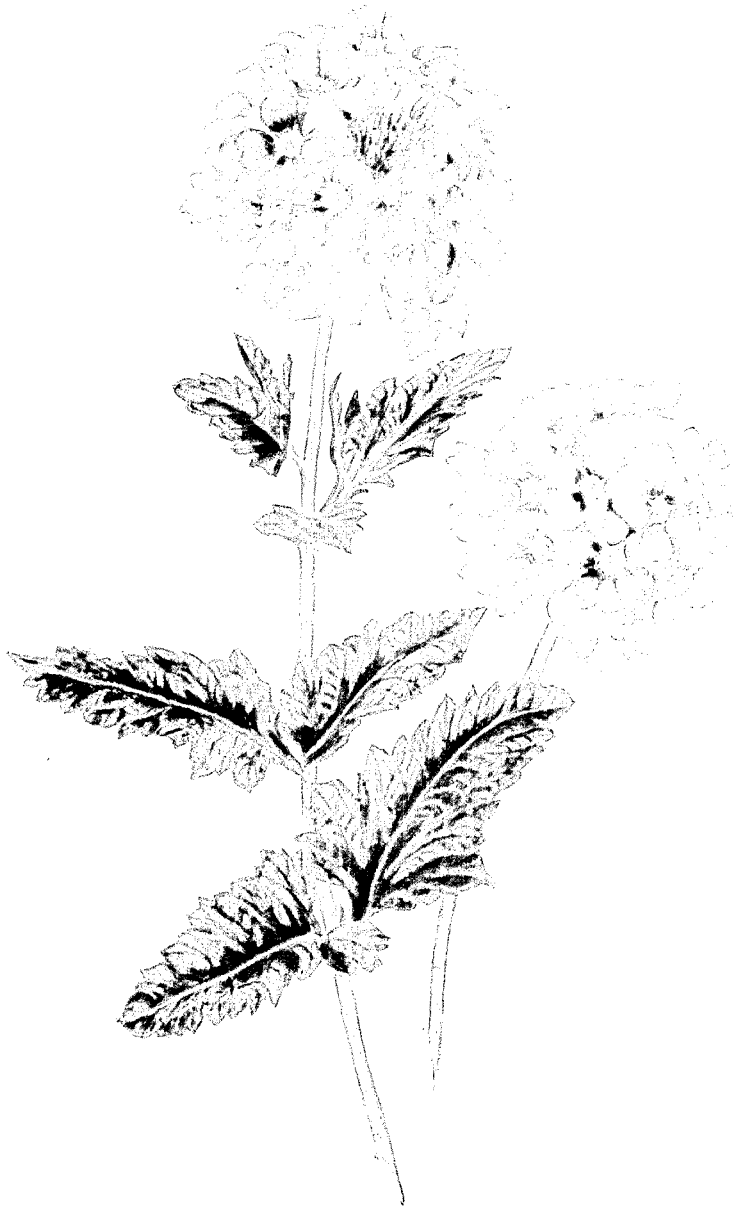
INVENTOR.
Florence Clyde Chandler
BY
Pennie, Edmonds, Morton, Barrows & Taylor
ATTORNEYS United States Patent Office Plant Pat. 1,334
Patented Dec. 21, 1954

1,334

MAGENTA VERBENA PLANT

Florence Clyde Chandler, Ardsley, N. Y., assignor to Boyce Thompson Institute for Plant Research, Inc., Yonkers, N. Y., a corporation of New York Application March 12, 1954, Serial No. 415,996

1 Claim. (Cl. 47—60)

This invention provides a new and distinct variety of magenta verbena plant. The new variety of plant is particularly characterized by its unique magenta flowers which are exceptionally large forming large clusters of many flowers borne on long, stiff stems, by large dark green leaves, by erect habit, by strong fragrance, and by good vigor. The new variety of plant has been reproduced asexually from cuttings, and the characteristics appear to be fixed.

The distinct variety of magenta verbena was produced by selecting a purple flowered plant growing in a bed of mixed verbena seedlings and propagating it vegetatively. This purple diploid was treated with colchicine and a purple tetraploid was obtained. This purple tetraploid seed parent with $2n=20$ chromosomes was crossed with a *Verbena hybrida,* Hort. Spectrum Red, which is a diploid with $2n=10$ chromosomes. The resulting new variety of plant is a triploid with $2n=15$ chromosomes obtained through hybridization.

The new variety of plant as thus originated was asexually reproduced from cuttings at Boyce Thompson Institute for Plant Research, Inc., Yonkers, New York.

In the accompanying drawing a plant of the invention is illustrated by a painting of a mature plant in substantially full bloom.

*Flowers*

The individual flowers are approximately ¾ inch in diameter, and each cluster is usually composed of from 45 to 55 flowers which are from 2¼ to 2½ inches in diameter and from 1¾ to 2½ inches in length. According to Ridgway's "Color Standards and Nomenclature," the freshly opened flowers have white centers with the remainder near dahlia purple changing to Schoenfields purple with age. According to Munsell the fresh flowers are RP 3/10 (red purple hue, value 3, chroma 10) changing to RP 4/12 with age. The flowers have strong fragrance. The flower clusters are borne on stiff stems about ⅛ inch in diameter, many of which are 22 inches long, which hold the clusters erect, usually about 18 inches above the ground.

*Leaves*

The leaves are dark green, thick, and range in width from 1 to 2 inches and in length from 2 to 3¼ inches near the base while the leaves at the tips of the branches are smaller.

*Seeds*

This new plant has produced no seeds to controlled self-pollinations and is propagated only by means of vegetative cuttings. The pollen is about 41% aborted and the grains are from 57 to 66.5 microns in diameter.

*General*

The new variety of plant covers the ground well and remains in excellent vegetative condition throughout the summer. This plant is more vigorous and robust than the old variety of Spectrum Red verbena and the leaves remain green and do not burn during the summer. The plant flowers well and has a profusion of bloom throughout the summer and until killed by frost.

I claim:

A new and distinct variety of magenta verbena plant substantially as illustrated and described, characterized by large individual magenta flowers in large clusters of many flowers borne on long, erect stems, by thick, large and dark green leaves, good vigor, and by profusion of bloom and strong fragrance.

No references cited.